United States Patent
Ma et al.

[11] Patent Number: 5,863,428
[45] Date of Patent: Jan. 26, 1999

[54] GUARD CARTRIDGE FOR CHROMATOGRAPHY

[75] Inventors: Qi-Feng Ma, Rancho Palos Verdes; Iraj Aghazade Mohandesi, Santa Monica; Fred Astani, Rancho Palos Verdes, all of Calif.

[73] Assignee: Phenomenex, Torrance, Calif.

[21] Appl. No.: 831,131

[22] Filed: Apr. 1, 1997

[51] Int. Cl.[6] .................................................. B01D 15/08
[52] U.S. Cl. ........................ 210/198.2; 210/656; 96/101
[58] Field of Search ................. 210/656, 198.2; 96/101; 422/70

[56] References Cited

U.S. PATENT DOCUMENTS

| | | | |
|---|---|---|---|
| 3,230,167 | 1/1966 | Golay | 210/198.2 |
| 3,583,230 | 6/1971 | Patterson | 210/198.2 |
| 4,026,803 | 5/1977 | Abrahams | 210/198.2 |
| 4,280,905 | 7/1981 | Gunkel | 210/198.2 |
| 4,283,280 | 8/1981 | Brownlee | 210/198.2 |
| 4,354,932 | 10/1982 | McNeil | 210/198.2 |
| 4,451,363 | 5/1984 | Brownlee et al. | 210/198.2 |
| 4,451,364 | 5/1984 | Higgins et al. | 210/198.2 |
| 4,451,365 | 5/1984 | Sattler | 210/198.2 |
| 4,457,846 | 7/1984 | Munk | 210/198.2 |
| 4,476,017 | 10/1984 | Scharff | 210/198.2 |
| 4,497,711 | 2/1985 | Shepherd | 210/198.2 |
| 4,563,275 | 1/1986 | McEachern | 210/198.2 |
| 4,565,632 | 1/1986 | Hatch | 210/198.2 |
| 4,636,316 | 1/1987 | Harris | 210/198.2 |
| 4,655,917 | 4/1987 | Schakelford | 210/198.2 |
| 4,692,243 | 9/1987 | Porsch | 210/198.2 |
| 4,710,289 | 12/1987 | Wermuth | 210/198.2 |
| 4,755,293 | 7/1988 | Sakamoto | 210/198.2 |
| 4,968,421 | 11/1990 | Spacek | 210/198.2 |
| 5,137,628 | 8/1992 | Hart | 210/198.2 |
| 5,324,427 | 6/1994 | Traveset-Masanes | 210/198.2 |
| 5,338,448 | 8/1994 | Gjerde et al. | 210/198.2 |
| 5,482,628 | 1/1996 | Schick | 210/198.2 |
| 5,525,303 | 6/1996 | Ford | 210/198.2 |
| 5,540,464 | 7/1996 | Picha | 210/198.2 |
| 5,595,653 | 1/1997 | Good | 210/198.2 |
| 5,601,785 | 2/1997 | Higden | 210/198.2 |
| 5,651,886 | 7/1997 | Hoffmann | 210/198.2 |
| 5,667,676 | 9/1997 | Alaska | 210/198.2 |
| 5,714,074 | 2/1998 | Karlsson | 210/198.2 |

*Primary Examiner*—Ernest G. Therkorn

[57] ABSTRACT

A new type of guard cartridge has been provided to prevent contamination of liquid chromatography (LC) columns by particulate and soluble contaminants. The cartridge is prepared by packing an empty tube with a chromatographic stationary phase and the packed tube is then sealed on both ends with porus sheets held in place by two collars. The cartridge gives minimum disturbance on column performance and significantly decreases the cost of production.

17 Claims, 4 Drawing Sheets

GUARD CARTRIDGE FOR CHROMATOGRAPHY

FIELD OF THE INVENTION

The present invention relates to liquid chromatography, specifically, relates to a means for protection of liquid chromatography columns from contamination by particulate and soluble contaminants.

BACKGROUND OF THE INVENTION

Liquid chromatography (LC) is a technique which employs a stationary phase and a liquid mobile phase to separate the solubilized components of a mixture into its various parts. A separation column generally consists of uniformly-packed small particles of stationary phase in a tube and the separation power of a separation column depends on the uniformity of the stationary phase. Particulate from the mobile phase and or samples can block flow passages formed from the interspaces of the packed stationary particles, causing high backpressures and disturbing the uniformity of stationary phase. Stationary phases have different surface chemistries and can irreversibly absorb some soluble components. The irreversible absorption will degrade the column capacity, disturb the uniformity of stationary phase, and increase column backpressure. Both irreversibly-absorbed soluble components and insoluble particulate will degrade column performance and reduce column life. A means for protecting liquid chromatography columns from contamination of particulate and soluble contaminants is critical for good performance and long service life of a separation column.

The most effective means to prevent column contamination is to place a guard device in front of a separation column. The guard device should allow analytes to pass through while retaining both particulate and soluble contaminants which would be adsorbed onto the column stationary phase irreversibly. For this reason, the guard device should have the same properties as the separation column. Though many types of guard devices exist in the market, they can be generally viewed as one special type of LC column packed with various stationary phases similar to that of the separation column. The guard device is a semi-disposable component of the liquid chromatography system and should be much less expensive.

Guard devices in liquid chromatography may be classified as guard columns, guard cartridges and guard discs according to the shape and the embodiment of the devices. A guard column refers to a device containing a short packed tube, a pair of frits on each end of the tube to hold the packing material in the tube white allowing liquid mobile phase to pass through, and two endfittings for fixing the frits and the tube together and for installation of the guard column between an injector and a separation column in a LC system. A guard cartridge contains a packed tube, a pair of frits on the ends of the tube to prevent the packing material from leaking out, and a means to keep the frits and the tube together. A guard cartridge usually contains no end fittings and a cartridge holder is needed in order to install the guard cartridge into chromatography flow line. A guard disc refers to a short guard cartridge and its commercially available form is a protection pad of stationary phases impregnated in PTFE (Teflon) matrix.

A guard column contains the same stationary phase as a separation column and is manufactured in the same way as the separation column. The only difference between a guard column and a separation column is the length-guard columns are short and separation columns are long. The production cost of a guard column is comparable to that of a separation column and renders guard columns the most expensive and the lest favorable protection means for separation columns.

Besides cost, guard columns may degrade the separation efficiency of separation columns. Column efficiency may be affected by the flow path taken when a guard column is used. Typically, the liquid mobile phase travels from a sample injection valve through a tube having a small inside diameter to the guard column which has a relatively large inside diameter, and then back to a connecting tube having a small inside diameter and finally to the separation column which again has a relatively large inside diameter. This change in diameter of the flow path produces a broadening effect on the sample zone and decreases overall column efficiency. The only way to overcome this effect is to place a guard device of the same diameter as the separation column in direct contact to the stationary phase of the separation column. The general configuration of guard columns makes this option impossible.

Guard columns contain chromatographic stationary phase and can retain samples slightly. This effect will change the retention time of the sample components. The change in retention time is a serious problem, especially for chromatography systems employing computer data acquisition systems. These systems rely on peak time windows to locate particular peaks. It also increases the difficulty of identifying certain components by matching their retention times to the published retention times in literature, which is an important technique for the characterization of unknown compounds.

In order to maintain their performance it is not recommended that guard columns be opened by users, The only way to determine the effectiveness of a guard column is by observing the chromatographic separation, such as peak broadening or retention time shifting. But chromatographic separations do not always indicate whether a guard column is adequately protecting a separation column. Contamination of a separation column can take place well before there are noticeable changes in plate number, pressure and resolution. Well-defined criteria for guard column replacement are missing.

Guard cartridges were developed as cost effective protection devices for separation columns. Guard cartridges need cartridge holders for in line installation. The functions of a guard device are divided between a guard cartridge and its cartridge holder. The guard cartridge removes contaminants and is a disposable part. The cartridge holder accommodates the cartridge and connects the cartridge in-line with the chromatography flow path. The cartridge holder is considered as a permanent part. In this way guard cartridges are simpler than guard columns and usually have no endfittings on their ends. However, they must have frits on both ends to retain the packing material. The frit design and its incorporation onto the packed cartridge is one of the most important considerations for guard cartridges. The frits should prevent packing material in the cartridge from leaking out; The frits should be permeable to the liquid mobile phase; The frits should be assembled onto the cartridge in such a way that once the guard cartridge is placed in a cartridge holder and installed in-line under high pressure, the liquid mobile phase should not leak out.

U.S. Pat. No. 5,482,628 describes a typical guard cartridge system which consists a cartridge and a holder. To prepare a guard cartridge, a tube of a given length is packed with the stationary phase. Two specialized frits, which comprise a porous center section and a plastic outer ring, are placed on the ends of the packed tube to hold the stationary phase in the tube and to permit the liquid mobile phase to pass through. The frits and the tube should have the same outer diameter. To fix the frits on the ends of the packed tube, a housing tube, or sleeve, is required. The housing tube has an internal diameter slightly smaller than the outer diameter of the packed tube. The two frits and the packed tube are forced and crimped into the housing tube. Though many types of frits have been used for guard cartridges, they all contain a porous center section permeable to liquid and a nonporous outer section for adequate sealing of the interface between the packed tube and the frits.

Though guard cartridges are more advantageous than guard columns from cost point of view, they still have many of the same limitations. Most guard cartridges are installed in the LC flow line in the same way as guard columns and suffer the diameter changes in flow path of liquid mobile phases as previously described; A used guard cartridge can not be opened to examine its effectiveness and no clear criteria or guidelines about when a guard cartridge should be replaced; Due to their configuration most guard cartridges are prepared 10 millimeters or longer in length and as such interfere with performance and retention time as previously described; The crimping process increases the possibilities for frit damage and leakage. Guard cartridges require relatively expensive frits of specific configuration which renders them more costly than a disposable item should be.

To overcome the limitations of guard columns and guard cartridges, a guard disc was invented and is described in U.S. Pat. No. 5,338,448. The guard discs are circular pads made of packing materials immobilized by membrane and are relatively inexpensive. The design allows the disc to be placed on the head of a separation column to eliminate flow disturbance. The stationary phase is the pad itself. The guard holder can be opened and the stationary phase can be visualized directly. If contaminants have color, the color change of the disc is an indication of its effectiveness. The disc is so thin that retention time for an analyte on a separation column will not be influenced. However, these discs are too thin, and a large portion of the disc mass is the impregnating membrane material itself. For this reason, the capacity of a guard disc is limited, which is a major disadvantage as a protection device. More importantly, the stationary phase of the disc has completely different physical structure from that of a packed guard column or a guard cartridge. In the case of the guard column or guard cartridge, the stationary phase is packed in a tube and the packed bed has microporous pores inside stationary particles and macro channels at the interspaces of the particles. The interspaces will range up to several micrometers. Particulate and soluble contaminants will stay on the surface of stationary particles and in the interspaces. Since the interspaces are large and will not be blocked completely by contaminants, the backpressure will not change very much after prolonged use. The pad disc is prepared by impregnating stationary particles into a PTFE membrane and the interspaces between the particles are filled with membrane polymer and are not available for liquid mobile phase to pass through. The only pores available for liquid flow are the micropores on the membrane which are very easily blocked. The consequence of the pad disc structure is rapid pressure build-up when contaminants block the surface pores of the pad membrane and cut off the flow passage for the liquid mobile phase. Though the pad disc still retains a large percentage of its initial adsorption capacity, it is not usable due to the resulting high backpressures. A special experiment showed that when the pad disc was placed in front a column and eluted with 50% acetonitrile, the pad backpressure increased from 1 bar to 100 bars within a few hours. However, a packed guard cartridge showed no significant change in backpressure under the same conditions.

As discussed above, there is a need to provide a guard device which does not significantly affect the efficiency or retention time of a chromatography column. The guard device should be able to be placed on the head of a chromatography column to minimize flow disturbance. It should be easy to examine the effectiveness of the guard device to ensure adequate protection of the separation column. Yet as a protection means the guard device must also have a reasonable capacity. Lastly, as a disposable element a guard device should be relatively inexpensive.

SUMMARY OF THE INVENTION

The objectives of the present invention are to provide:

an inexpensive means for protection of chromatography columns.

a guard device which does not significantly influence the performance of a chromatography column, e.g. retention time, plate number and resolution.

a guard device whose stationary phase can be easily inspected for effectiveness.

a guard device which can be used either with a holder or placed directly on the column head.

a guard device with good decontamination capacity.

In the present invention, a chromatographic stationary phase is packed into a tube and held in the tube by two porus sheets on both ends of the tube. The porous sheets are stretched to form a smooth surface and are fixed on the ends of the tube by two collars. The finished products can be installed in a guard cartridge holder or placed on the head of a LC column to protect the LC column from contamination of particulate and irreversibly adsorbed components.

DETAILED DESCRIPTION OF THE PREFERRED EMBODIMENT

Figure 2A:
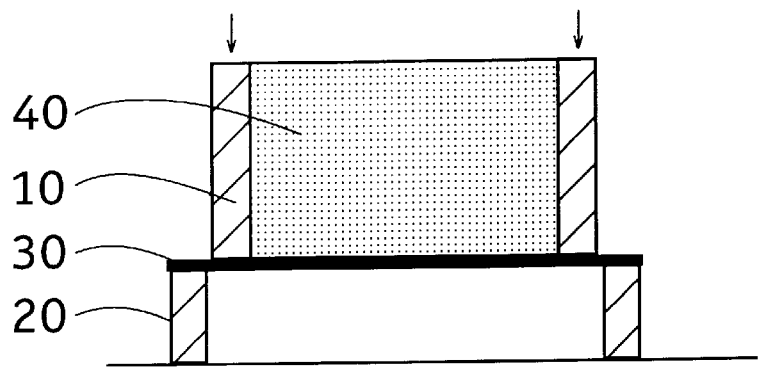
FIGS. 2a, 2b, and 2c are cross-sectional views illustrating the assembly process of the guard cartridge.
Figure 2B:
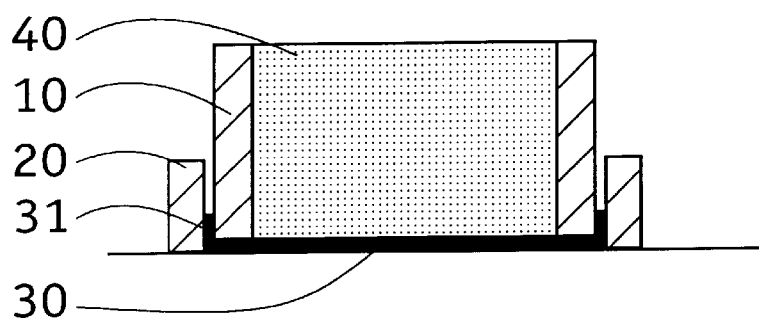
Figure 2C:
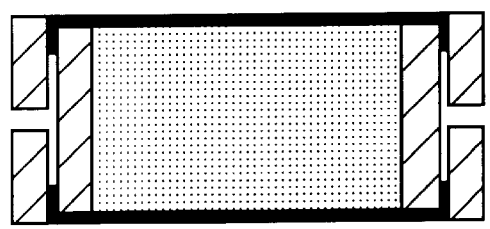

Referring to FIGS. 2a, 2b, and 2c the preferred embodiment of the present invention comprises cartridge body 10, collars 20, porous sheet 30, and stationary phase 40. cartridge body 10 is about several millimeters to centimeters high and is made preferably of rigid materials such as PEEK or stainless steel. Collar 20 is a rigid or semi-rigid ring. The height of collar 20 is the same as, or less than half of the height of cartridge body 10 and the internal diameter of collar 20 is slightly larger than the outer diameter of cartridge body 10. Collar 20 is made of rigid or semi-rigid material such as plastic and metal. Porous sheet 30 is a circular disc which has diameter a few millimeters larger than the outer diameter of cartridge body 10. Porous sheet 30 is preferably made of plastic, clothe fiber, or metal screens.

Figure 1:
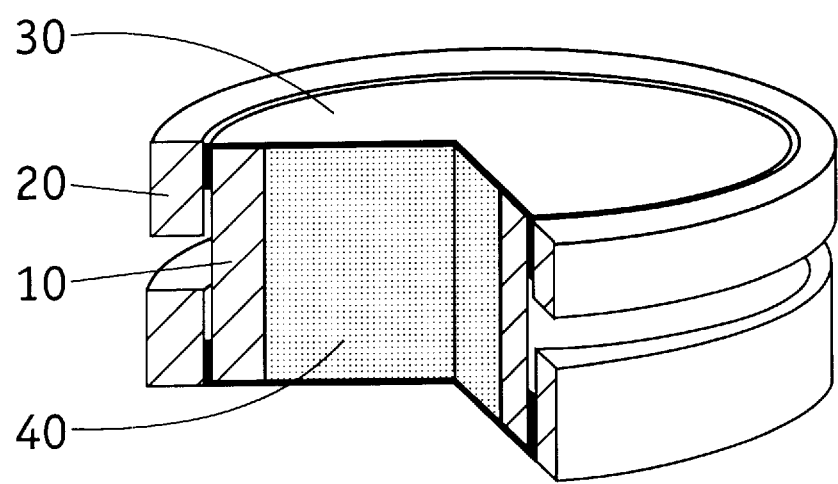
FIG. 1 is an exploded view of the guard cartridge in the present invention.

To prepare a guard cartridge as illustrated in FIG. 2a, cartridge body 10 is packed with stationary phase 40 by conventional methods. Collar 20 is placed on a flat base and sheet 30 is laid concentrically on the top of the collar. The packed cartridge body 10 is placed concentrically on sheet 30 and pressure is applied to cartridge body 10 to press cartridge body 10 and sheet 30 into collar 20. Sheet 30 is stretched out during press and fixed tightly on the end of cartridge body 10 by collar 20. The fixing is accomplished by folding edge 31 of circular sheet 30 between collar 20 and cartridge body 10 (FIG. 2*b*). The other end of packed cartridge body 10 is sealed with sheet 30 in the same way to obtain a finished guard cartridge (FIG. 2*c*, FIG. 1).

Figure 3:
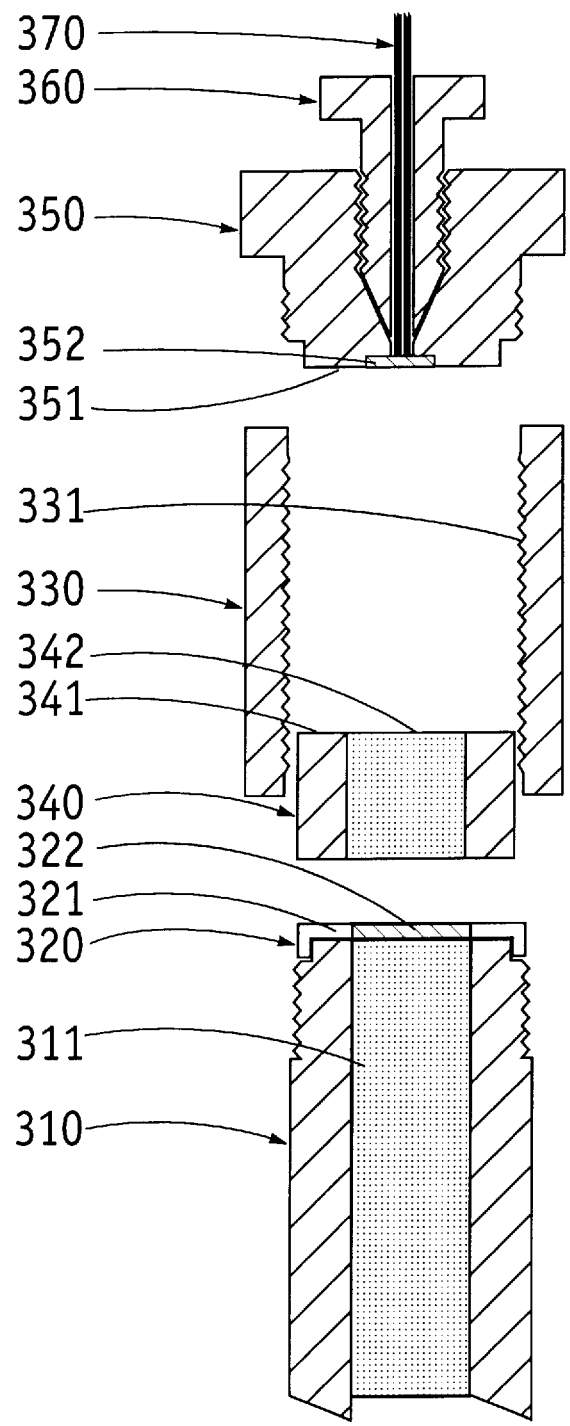
FIG. 3 is a cross-sectional view illustrating direct installation of the guard cartridge on the head of a chromatography column.

FIG. 3 shows an embodiment in which the guard cartridge is in direct contact with the top portion of a chromatographic separation column. The top of column 310 is capped by Frit 320. Frit 320 comprises porous portion 322 and non-porous portion 321. Non-porous portion 321 is a collar of cap shape and is preferably made of rigid plastic, such as PEEK, Teflon, or Delrin. The porous portion 322 is sealably integrated in the center of non-porous portion 321 and directly contacts stationary phase 311. Coupler 330 threads onto column 310. Guard cartridge 340 is then placed into the cavity of coupler 330 and held in place by threading endfitting 350 into coupler 330. After tightening, flat end 351 of endfitting 350, supporting portion 341 of guard cartridge 340, non-porous portion 321 of frit 320, and the top of support portion of column 310 sealably contact each other, preventing liquid mobile phase from leaking. Tubing 370 is attached to endfitting 350 by end nut 360. Liquid mobile phase and samples come from tubing 370, pass through frit 352 of endfitting 350, stationary phase 342 of guard cartridge 340, and porus portion 322 of frit 320, and enter stationary phase 311 of LC column 310. Contaminants will be retained by the guard cartridge while samples goes into separation column for separation. Once a guard cartridge losses its effectiveness, coupler 330 is detached from column 310 and a new guard cartridge is installed. Cap-shaped frit 320 should never be removed from column 310 during this process for protection of the uniformity of stationary phase 311 of separation column 310.

Figure 4:
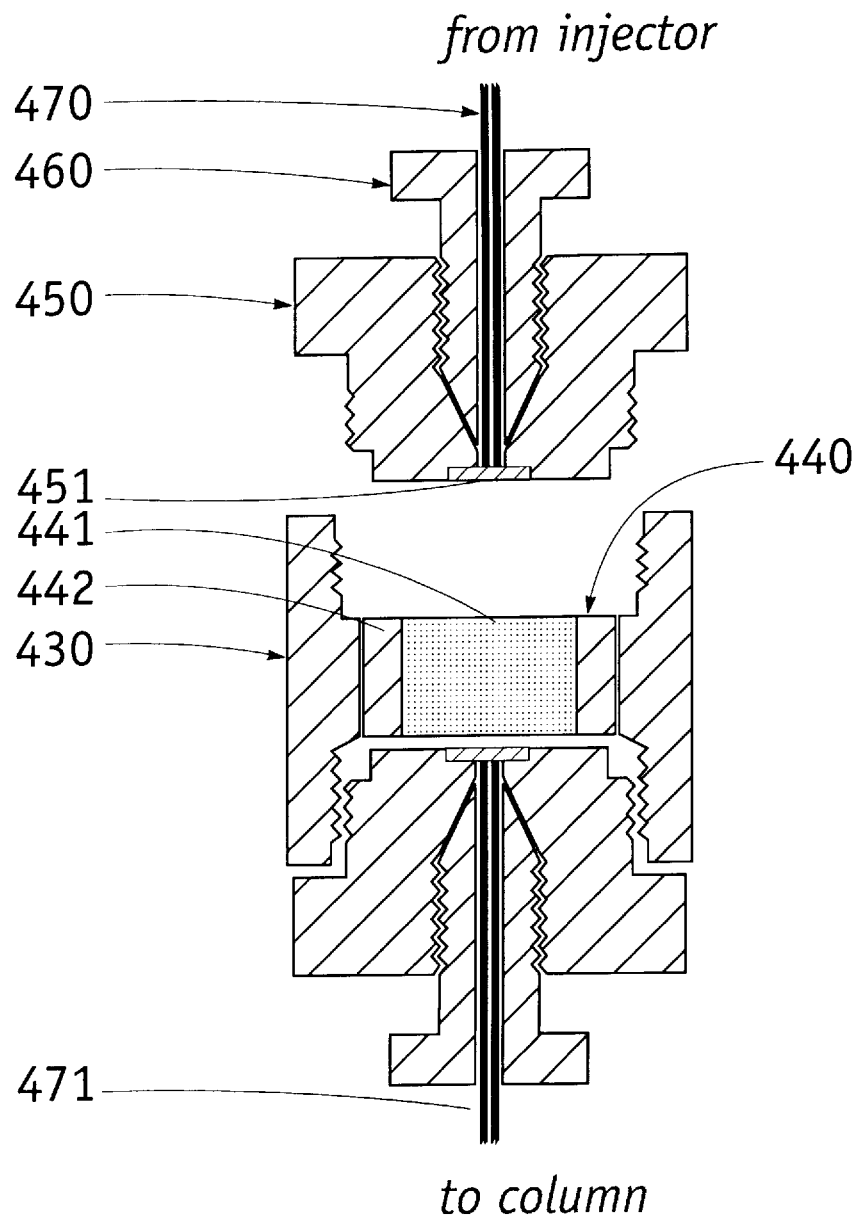
FIG. 4 is a cross-sectional view illustrating the installation of the guard cartridge in a conventional cartridge holder.

FIG. 4 schematically depicts a universal way for installation of the guard cartridge of the present invention. A classical cartridge holder is used for accommodation of the guard cartridge and for installation of the guard cartridge in the flow path of a LC system. The holder comprises coupler 430 and endfitting 450. Endfitting 450 is integrated with a frit 451 at its center. Guard disc 440 is sealably secured in the center of coupler 430 by tightening endfittings 450 into coupler 430 from opposing sides. Mobile phase flows from inlet 470, passes through frit 451, enters stationary phase 441 of guard cartridge 440 where contaminants are retained, and is directed into the separation column by outlet tube 471.

As one major feature of the present invention, thin porous sheets are used to hold the packing material in the cartridge and the sheets are fixed by two collars on the lateral wall of the cartridge body. This feature clearly distinguish the present invention from conventional guard cartridges as described in U.S. Pat. No. 5,482,268 and the guard disc described in U.S. Pat. No. 5,338,448. Physically, the present invention differs substantially from the prior arts. Conventional guard cartridges utilize rigid thick frits to enclose the stationary phases. The guard discs have no frits and the stationary phases are impregnated in plastic membrane. As mentioned in line 24, column 9 of U.S. Pat. No. 5,338,448, the guard disc of the prior art does not contain free bulk particulate stationary material. The guard cartridge in the present invention has free bulk stationary material but no thick rigid frits. Thin flexible porous sheets replace the frits. When a plastic porous sheet is used, the center of the circular sheet contacts with packing materials in the cartridge body. When the guard cartridge is installed in a guard holder or on the inlet end of a column, the porosity on the center portion of the sheet still remains, enabling liquid to flow through. The outer portion of the sheet is located between rigid surfaces of the endfitting and the end of the packed cartridge body and become a sealing gasket after tightening the endfitting. The finding that a plastic porous sheet can function both as a frit and a sealing gasket greatly simplifies the production process of guard cartridges and significantly decreases production cost.

Existing frits for guard cartridges are thick rigid circular discs, which consist of porus central section and non-porus annular ring. The interface between the two sections is a potential cause of flow disturbance. In the present invention porous thin sheets replace conventional frits and provide an even surface on the ends of the guard cartridge. The flat ends will result in an uniform flow path so that better performance is expected. Besides, thin sheets have less void volume than thick conventional frits, which is beneficial for separation.

The length of guard cartridges in the present invention can be adjusted in such a way that the guard cartridges can provide adequate protection for a separation column while having no significant influence on retention time of the separation column. Commercially available guard columns and cartridges are typically over 1 cm long and will affect retention time of a separation column. To eliminate this effect an alternative design utilizing a thin adsorbent-impregnating plastic pad is employed as a protective means for the chromatography column. As mentioned previously, the pad is less than one millimeter thick and no retention time increase is observed. However, the pad is too thin and the capacity is low. Utilizing a thick pad will increase backpressure. Besides, the nature of a membrane renders the pad very susceptible to blockage and the pad has to be changed frequently. The guard cartridges of the present invention are packed with stationary phase particles and the channels formed from the interspaces of packed particles are much larger than the pores of membrane pads and will not be blocked easily. This represents a significant advantage over the membrane pads. The process and the components for guard cartridge preparation in the present invention also allow very short cartridges to be made, which is superior to the conventional guard columns and guard cartridges for reasons previously described.

If white plastic porous sheets are used for the preparation of guard cartridges in the present invention, color changes in the packing bed of the guard cartridges can be easily observed. This adds another advantage over conventional guard cartridges. The cartridges in the present invention can be taken out from the holder and the outlet end can be examined visually. Usually contaminants will change the color of the packing bed. If the packing bed on the outlet of a guard cartridge shows color change, the cartridge should be replaced by a new one.

Another major feature of the present invention is that the guard cartridge can be placed on the head of a separation column to minimize flow disturbance. FIG. 3 depict the preferred embodiment. The unique design in FIG. 3 has several advantages. First, the diameter of the flow path for liquid mobile phase does not change when the liquid enters stationary phase 311 of chromatography column 310 from stationary phase 342 of guard cartridge 340. The influence of changing flow paths on column performance is eliminated. In fact, when a guard cartridge is installed in this way, the separation parameters, such as retention time, plate number and peak symmetry remain the same as that when the chromatography column is used alone. Second, cap-shaped frit 320 provides adequate protection of stationary phase 311 of column 310. A regular chromatography column is not recommended to be opened by users due to the possibility of touching the surface of stationary bed and changing its uniformity. With the design in FIG. 3, the stationary phase 311 of column 310 is covered by cap-shaped frit 320 which makes guard cartridge change a worry-free process. Besides, the assembly and disassembly are very simple and can be accomplished by an unskilled worker.

Many modifications and variations besides the embodiments specifically mentioned may be made in techniques and structures without departing substantially from the concept of the present invention. Accordingly, it should be clearly understood that the form of the invention described and illustrated herein is exemplary only, and is not intended as a limitation on the scope thereof.

What is claimed is:

1. A cartridge assembly for protection of chromatography columns from contamination comprising:
    a cartridge body of hollow cylinder having a central passage, a lateral wall, and a pair of ends;
    particles being filled within said central passage of said cartridge body;
    a pair of circular collars having an internal diameter slightly larger than the outer diameter of said cartridge body and a height the same as, or shorter than half of the height of said cartridge body;
    a pair of circular flexible porous sheets having a diameter 0.1 to 20 mm larger than the outer diameter of said cartridge body;
    an assembled cartridge with said particles entrapped within said central passage of said cartridge body by said porous sheets which are fixed at said ends of said cartridge body by sandwiching the edge of said sheet between the interior wall of said collar and the exterior wall of said cartridge body.

2. A cartridge assembly of claim 1 wherein said assembled cartridge is installed in a holder which is then connected onto the inlet of a chromatography column.

3. A cartridge assembly of claim 1 wherein said assembled cartridge is installed directly onto the inlet end of a chromatography column and is in direct contact with the frit on the end of said chromatography column.

4. A cartridge assembly of claim 1 wherein said cartridge is assembled by:
    packing said particles in said central passage of said cartridge body;
    centrically laying said porous sheet on one end of said packed cartridge body;
    centrically placing said collar on said porous sheet;
    pressing said collar against said packed cartridge body so that said sheet is stretched out by collar movement to form a smooth surface at the end of said packed cartridge body and the edge of said sheet is sandwiched between said collar and said packed cartridge body;
    repeating the process to close another end of said packed cartridge body with said sheet.

5. A cartridge assembly of claim 1 wherein said cartridge is assembled by:
    centrically laying said porous sheet on one end of said cartridge body;
    centrically placing said collar on said porous sheet;
    pressing said collar against said cartridge body so that said sheet is stretched out to form a smooth surface by collar movement and the edge of said sheet is sandwiched between said collar and said cartridge body;
    filling said cartridge body with particles;
    repeating the process to enclose another end of the particles-filled cartridge body with said sheet.

6. A cartridge assembly of claim 1 wherein said porous sheet has pore size ranging from 0.01 to 100 micrometer.

7. A cartridge assembly of claim 1 wherein said porous sheet has a thickness ranging from 0.01 to 1 millimeter.

8. A cartridge assembly of claim 1 wherein said porous sheet is made of plastic.

9. A cartridge assembly of claim 8 wherein said porous sheet is made of polypropylene.

10. A cartridge assembly of claim 1 wherein said porous sheet is made of metal.

11. A cartridge assembly of claim 1 wherein said porous sheet is made of natural fiber.

12. A cartridge assembly of claim 1 wherein said collar and said cartridge body are made of any rigid material.

13. A cartridge assembly of claim 1 wherein said collar and said cartridge body are made of any semi-rigid material.

14. A cartridge assembly of claim 1 wherein sad particles are chromatographic packing material.

15. A cartridge assembly of claim 1 wherein said cartridge is used as a protection means for chromatography columns.

16. A cartridge assembly of claim 1 wherein said cartridge is used as a filter.

17. A cartridge assembly of claim 1 wherein said cartridge is used for sample treatment.

* * * * *